US008611499B2

(12) United States Patent
Spahn

(10) Patent No.: US 8,611,499 B2
(45) Date of Patent: Dec. 17, 2013

(54) METHOD FOR MONITORING THE X-RAY DOSAGE ADMINISTERED TO A PATIENT BY A RADIATION SOURCE WHEN USING AN X-RAY DEVICE, AND X-RAY DEVICE

(75) Inventor: Martin Spahn, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 312 days.

(21) Appl. No.: 12/780,023

(22) Filed: May 14, 2010

(65) Prior Publication Data

US 2010/0290591 A1 Nov. 18, 2010

(30) Foreign Application Priority Data

May 14, 2009 (DE) .......................... 10 2009 021 239

(51) Int. Cl.
*H05G 1/26* (2006.01)
*H05G 1/64* (2006.01)
*G01N 23/04* (2006.01)
*G01N 23/083* (2006.01)

(52) U.S. Cl.
USPC ............... 378/98.5; 378/63; 378/97; 378/901

(58) Field of Classification Search
USPC .......... 378/4–20, 62, 63, 65, 91, 97, 98, 98.5, 378/162, 165, 207, 210, 901; 600/425–429; 382/123, 130–132, 168; 250/370.07
See application file for complete search history.

(56) References Cited

U.S. PATENT DOCUMENTS

| | | | |
|---|---|---|---|
| 6,292,537 B1 | 9/2001 | Zimmermann | |
| 6,360,116 B1* | 3/2002 | Jackson et al. | 600/427 |
| 6,650,930 B2* | 11/2003 | Ding | 600/436 |
| 7,343,030 B2* | 3/2008 | Sawyer | 382/128 |
| 2002/0131552 A1 | 9/2002 | Nishizawa et al. | |
| 2004/0228443 A1* | 11/2004 | Bohm et al. | 378/97 |
| 2006/0050840 A1* | 3/2006 | Ikeda et al. | 378/8 |
| 2007/0041499 A1* | 2/2007 | Lu et al. | 378/65 |
| 2007/0053480 A1* | 3/2007 | Nishide et al. | 378/4 |
| 2009/0175418 A1* | 7/2009 | Sakurai et al. | 378/98.5 |
| 2009/0234175 A1* | 9/2009 | Maier | 600/3 |
| 2009/0252291 A1* | 10/2009 | Lu et al. | 378/65 |

FOREIGN PATENT DOCUMENTS

| | | |
|---|---|---|
| AT | 505355 A1 | 12/2008 |
| DE | 19730519 A1 | 1/1999 |
| DE | 19903749 A1 | 8/2000 |
| DE | 10153864 A1 | 10/2002 |
| DE | 102005028415 A1 | 12/2006 |

* cited by examiner

*Primary Examiner* — Anastasia Midkiff

(57) ABSTRACT

A method for monitoring the X-ray dosage administered to a patient by a radiation source when using an X-ray device is proposed. The X-ray device is in particular a C-arm X-ray device. A location-dependent dosage value on the surface of the patient is determined with reference to parameters which describe the recording geometry and the radiation that is administered. The surface is described by a patient model in particular. A representation of the dosage value and/or of a value derived therefrom is displayed.

19 Claims, 2 Drawing Sheets

METHOD FOR MONITORING THE X-RAY DOSAGE ADMINISTERED TO A PATIENT BY A RADIATION SOURCE WHEN USING AN X-RAY DEVICE, AND X-RAY DEVICE

CROSS REFERENCE TO RELATED APPLICATIONS

This application claims priority of German application No. 10 2009 021 239.6 filed May 14, 2009, which is incorporated by reference herein in its entirety.

FIELD OF THE INVENTION

The invention relates to a method for monitoring the X-ray dosage administered to a patient by a radiation source when using an X-ray device, in particular a C-arm X-ray device, and an associated X-ray device.

BACKGROUND OF THE INVENTION

X-ray devices of various types are well known and are used for the purpose of diagnostic examination, but are also used for monitoring interventions in the context of e.g. cardiology, radiology and neurosurgery. Use is often made of C-arm X-ray devices comprising at least one C-arm, on which a radiation source and a detector are arranged facing each other, a high-voltage generator for generating the X-ray voltage of the radiation source, an imaging system including a display device, a control device, and a patient couch which features a patient support plate on which a patient who is to be examined can be supported.

In particular, the skin on the side oriented towards the radiation source is exposed to dosages of X-ray radiation, since the soft parts of the X-ray spectrum are absorbed there. It should be noted in this case that, when monitoring interventions, the exposure typically tends to be higher because the interventions are lengthy and the projection angle at which the X-ray images are recorded changes little in this context, and therefore the position of the radiation source likewise undergoes little change and the same skin section is exposed to X-ray radiation. However, diagnostic examinations (in particular three-dimensional applications) which use higher dosages than fluoroscopy also contribute to the skin dosage.

It is therefore common today to specify the dosage area product and/or the total dosage, in order that a person conducting an examination, e.g. a radiologist, cardiologist or surgeon, can estimate the exposure of the patient. Disadvantageously, however, this information is often insufficient because it reveals very little about the presence of especially exposed regions on the skin of a patient, in particular.

SUMMARY OF THE INVENTION

The invention therefore addresses the problem of specifying a method by means of which the dosage exposure of a patient can be made known more effectively to a person conducting an examination.

For the purpose of solving this problem, with reference to parameters which describe the recording geometry and the radiation that is administered, a method of the type cited in the introduction inventively provides for determining a location-dependent dosage value on the surface of the patient, said surface being described by a patient model in particular, and for displaying a representation of the dosage value and/or of a value derived therefrom.

The invention therefore proposes, by means of measurement and/or from the settings of the X-ray device, to determine the technical parameters which describe the recording geometry and the radiation that is administered. If the recording geometry and the radiation characteristics are known, it is possible to determine a location-dependent dosage value (the skin dosage) on the surface of the patient. In particular, a patient model can be used for this purpose. On the basis of this location-dependent dosage value, it is possible to generate and display a representation of the dosage value and/or of a value that is derived therefrom. The person conducting an examination is therefore presented with location-specific information concerning the extent to which the skin of the patient receives a dosage as a result of the activity of the radiation source, and therefore e.g. excessive exposure or exposure in sensitive regions can be identified well in advance and avoided. An improved resource is therefore made available to the doctor, in order that the dosage exposure of the skin of the patient can also be taken into consideration in the context of the recording plan.

It should be noted at this point that the method can obviously also be used in X-ray devices featuring a plurality of radiation sources, the recording geometry and the radiation that is administered being then determined in respect of each of the radiation sources, and taken into consideration when determining the location-dependent dosage value. In particular, biplanar systems should be cited in this context.

On the basis of the parameters describing the recording geometry, it is possible to determine e.g. a relative position and relative orientation of patient and radiation source, and a radiation fan beam of the radiation source. While the relative position describes the distance of the patient from the radiation source, the relative orientation is required in order to show the direction in which the patient is irradiated by the radiation source. Finally, the radiation fan beam specifies the opening angle, i.e. it ultimately defines which area on the patient is irradiated. To the extent that it is required for determining the irradiated skin surface, the recording geometry is then known. A distinguishing point of the patient or of the patient model can serve as a reference in this case, in order to determine the presence of irradiation. Consideration is also given to the parameter or parameters describing the radiation that is administered, thus allowing a location-specific dosage value (skin dosage) to be determined. In order to achieve this in practice, provision can be made for subdividing the radiation fan beam of the radiation source and/or the irradiated surface of the patient into subregions, for which a dosage value is then ascertained in each case, thereby producing an overall dosage value which is distributed by location.

If the above cited variables (relative position and orientation of patient to radiation source, radiation fan beam of the radiation source) and the at least one parameter describing the radiation that is administered are known, it is possible to determine a location-dependent dosage value using the $1/R^2$ law, where R is the average distance from the focus of the radiation source (e.g. anode plate) to the surface of the patient (this being given by the current recording geometry and the patient model), and the radiation characteristics of the radiation source.

In terms of parameters describing the recording geometry, it is possible to determine e.g. the position and orientation of the radiation source and/or the opening angle of the radiation source and/or a collimation of the radiation source and/or the position and/or orientation of a patient support plate relative to the radiation source and/or the position and/or orientation of the patient and/or the surface of the patient. In this case, the orientation of the radiation source corresponds essentially to the projection direction which, like the position of the radiation source, is generally stored in the control device of the X-ray device in any case; the opening angle or opening angles of the radiation source can describe the radiation fan beam of the radiation source, in particular with reference to a collimation. In particular, provision can be made for the position and orientation of the patient to be determined in the same system of coordinates as the position and orientation of the radiation source, this being possible e.g. if provision is made for a measuring means (e.g. a camera and/or ultrasound) which is fixed relative to the radiation source, such that the calibration of the measuring means relative to the radiation source is known. In another embodiment, a position and orientation of the patient relative to a patient support plate can be determined and/or assumed, the relative position of patient support plate and radiation source being derived from an internal calibration of the X-ray device. In fact, a control device of an X-ray device usually knows how the radiation source relates to the patient support plate. In particular, a misalignment of the patient support plate or similar can also be taken into consideration in this case. In order that the recording geometry relating to the patient can now be determined, it is therefore only necessary additionally to know how the patient is positioned on the patient support plate, which can again be e.g. determined using a measuring means and/or with reference to recording parameters, e.g. an orientation of the patient as entered at the start of the examination, but can also (possibly additionally) be derived or assumed. For example, it is possible to use the assumption that the patient is arranged centrically in a specific orientation on the patient support plate. Using a simple patient model and on the basis of such an assumption, which is optionally modified further by the analysis of recording parameters, it is already possible to determine a local skin dosage, i.e. a location-dependent dosage value, without further measurement of the patient.

As discussed above, for the purpose of the invention, the parameters can at least be partially measured and/or derived from recording parameters. Recording parameters, i.e. parameters which define the image recording, can therefore additionally comprise e.g. the direction in which the head of the patient is arranged on the patient support plate or similar. The position and orientation of the radiation source for the image recording can also be derived from the recording parameters, as can filter settings, collimator settings, etc. In particular, however, provision can be made for dosage characteristics of the radiation source for a recording to be determined automatically from an operating voltage of the radiation source, a total current of the radiation source and, if filtering is present, from a prefiltering parameter. The dosage that is emitted by the radiation source (e.g. comprising an X-ray tube) and optionally its spectral distribution can be ascertained from the operating voltage of the radiation source and the total current. If filtering is provided, however, it is also important to consider any influences of this filter, wherein said influences can be represented by a prefiltering parameter. The spectrum for specific recordings is also often known in advance, such that dosage characteristics can be modeled directly therefrom. As an alternative to ascertaining the dosage characteristics in the manner described above, provision can also be made for measuring a dosage area product using a measuring device which is arranged at the radiation source. Measuring devices for measuring a dosage area product are often already provided with X-ray devices and can also be used for the method according to the invention. The dosage area product is particularly suitable for determining the location-dependent dosage value, since the location-dependent dosage value can then be determined simply by dividing the dosage area product by the irradiated area.

As mentioned above, an advantageous embodiment of the present invention can also provide for the position and/or orientation of the patient, possibly relative to a patient support plate or also directly relative to the radiation source, to be measured optically, in particular by means of a camera and/or by means of ultrasound. It should already be noted at this point that such measured values/images, obtained using a measuring means, can obviously also be used for creating and/or adapting the patient model (if available) or for ascertaining the surface of the patient.

As described above, a patient model can be used particularly advantageously to describe the surface of the patient. In a simple embodiment, provision can be made for the patient model to comprise at least one cylinder and/or ellipsoid in this case. For example, various limbs, the torso and the head of the patient can be depicted as cylinders and/or ellipsoids in each case.

In a further preferred embodiment, the patient model can be adapted with reference to patient-specific information, in particular the size and/or weight and/or sex and/or age. The patient model can be expanded for larger and heavier patients, for example, and shaped for variations in sex, for example. Such patient-specific information can be obtained e.g. from an information system, in particular a radiology information system (RIS) and/or a patient registration. If the patient is indeed registered in the information system and/or at the X-ray device, such data is generally retrieved in any case, and therefore patient-specific adaptation of a model can be carried out.

However, as mentioned above, it should be noted that it is obviously also possible to use data obtained from a measuring means, in particular a camera and/or ultrasound sensor technology, for creating and/or adapting the patient model. A patient model can also be generated or adapted individually in this way, in order to manage the received dosage information more accurately.

When carrying out a plurality of recordings, it is advantageously possible to determine a location-dependent total dosage value as a sum of the dosage values for individual recordings and to show the total dosage value. If a repeated recording of X-ray images is intended/performed in a recording series or in the context of fluoroscopy, for example, it is therefore possible to ascertain a location-dependent total dosage value which expresses the skin dosage for all previous and/or planned recordings. In an effective further embodiment, it is also possible in this context to provide for movements of the patient between the recordings to be determined and taken into consideration. For this purpose, it is possible to use e.g. the above cited measuring means, in particular a camera and/or ultrasound sensors, by virtue of which the position and orientation of the patient can be tracked during the entire examination or intervention, in order that the ascertained dosage value can be updated and/or a previously ascertained dosage value can be adapted if applicable.

Using the method according to the invention, it is also possible to provide a breakdown according to various parts of the X-ray spectrum. As mentioned in the introduction, in particular the soft part of the X-ray spectrum is absorbed on the skin surface. Provision can therefore be made for at least two location-dependent dosage values to be determined and shown for various radiation energies and/or radiation energy ranges. This allows the skin dosage to be broken down even more accurately. In particular, an average energy of the radiation occurring at the location on the surface of the patient can also be determined and displayed as a derived value in this case. In this case, it is particularly advantageous if a plurality of representations can be generated and, in particular, shown concurrently.

In general, the representation can comprise a view from the current irradiation direction and/or the irradiation direction of the current recording. This means that e.g. the dosage value (the skin dosage) can always be shown by default initially from the direction which is given by the momentary projection direction and/or the momentary setting of the X-ray device, in particular of the C-arm. As described above, this is given by the position of radiation source and detector relative to the patient support plate. In the case of the biplanar X-ray device mentioned above, provision can also be made for a representation from both projection directions to be displayed. Provision can be made for the representation to be adapted automatically if the position and/or orientation of the radiation source is adapted, e.g. by means of an operating device, meaning that in the event of a movement of the C-aim, for example, the representation is immediately adapted to the new irradiation direction.

Alternatively or additionally, provision can be made for a viewing direction of the representation to be changed by a user, in particular by means of an operating element. A joystick or mouse is particularly suitable for this purpose, in order to change the "virtual irradiation direction", such that the entire surface of the patient can be examined.

Of course, any types of representation are generally possible, e.g. three-dimensional (e.g. rendered) representations etc. in addition to projections.

In a particularly effective embodiment of the present invention, provision can be made for the representation of the dosage value to be color-coded. Such a representation can also be referred to as a spectral representation. In this context, provision can be made for places of high skin dosage to be coded red, for example, and places of low skin dosage to be coded blue. In this way, it is possible to provide a representation which is particularly comprehensible and quick to grasp.

As indicated above, the method according to the invention allows the location-dependent dosage value (in particular therefore the total dosage value) and the representation to be established essentially in real time, meaning that the values and the representation are updated correspondingly whenever a new X-ray recording is effected. However, it is obviously also conceivable to determine a first estimate/determination of the exposure of the skin already in the context of the recording plan, by already determining and representing dosage values/total dosage values in advance. In a combined version, it is obviously also conceivable always to already take into consideration the next image that is to be recorded. Any chosen configuration is possible here, in order to ensure that the user is offered the best possible information that is needed.

In addition to the method, the present invention also relates to an X-ray device comprising in particular a radiation source which is arranged on a C-arm, a radiation detector, a patient support plate, a display device and a control device which is designed for performing the method according to the invention. Using such an X-ray device, it is therefore possible to determine and display location-dependent dosage values or values derived therefrom on the surface of a patient, either in real time and/or calculated in advance, in order thus to give the person conducting an examination a better instrument for assessing the exposure of the patient. Consequently, the user can perform a better evaluation and possibly optimize their mode of working with reference to the previously applied skin dosage, e.g. change the projection direction, invert the projection—transpose the positions of radiation source and radiation detector—or utilize low-dosage diagnostic programs where this is sufficient for the recording to be carried out.

Of course, all of the embodiments relating to the inventive method can also be transferred to the X-ray device; in particular, the X-ray device according to the invention can also comprise various measuring means in order to allow the parameters to be ascertained.

BRIEF DESCRIPTION OF THE DRAWINGS

Further advantages and details of the present invention are derived from the exemplary embodiments described below and with reference to the drawings, in which.

DETAILED DESCRIPTION OF THE INVENTION

Figure 1:
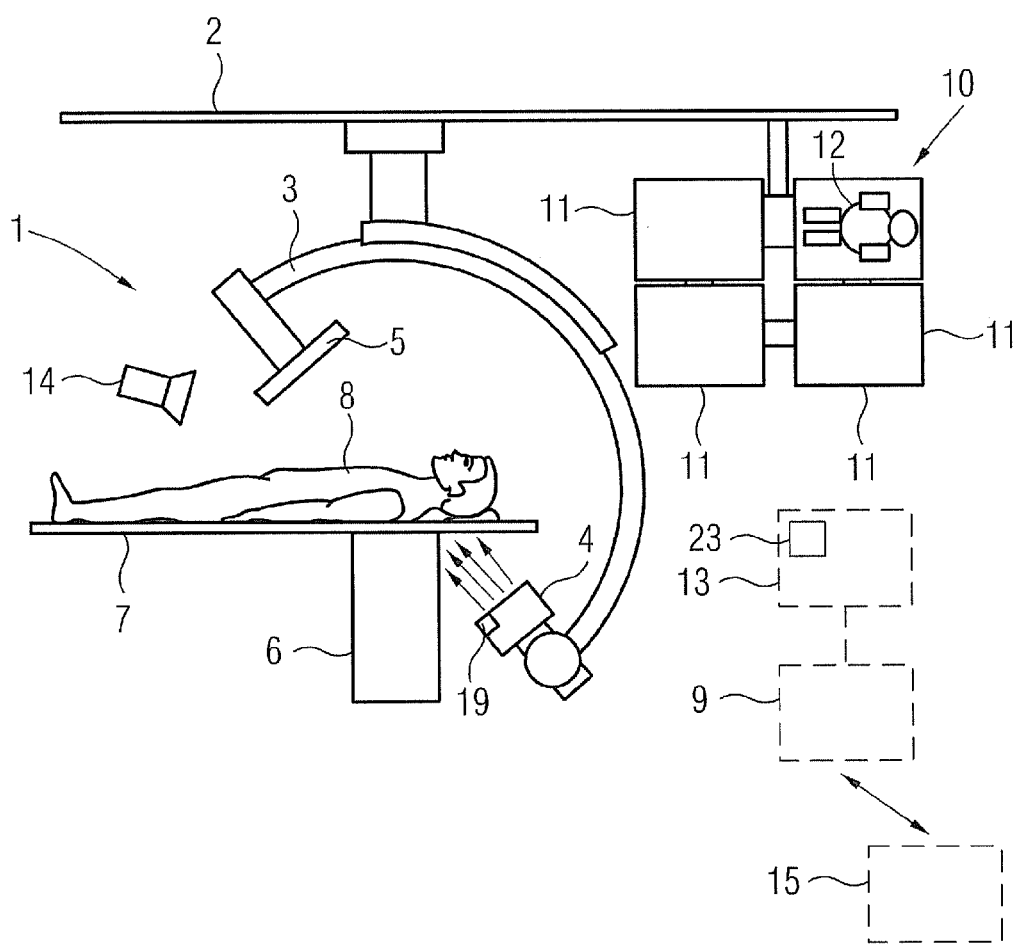
FIG. 1 shows an X-ray device according to the invention.

FIG. 1 shows an X-ray device 1 according to the invention, specifically a C-arm X-ray device in this case. It comprises a C-arm 3, this being attached to a ceiling 2 in the present example, on which a radiation source 4 (X-ray tube) and a radiation detector 5 (e.g. a semiconductor radiation detector) are arranged facing each other. The C-arm 3 is movable, in particular rotatable, relative to a patient couch 6 comprising a patient support plate 7 on which a patient 8 can be positioned for examination. The X-ray device 1 further comprises a control device 9 which is only shown schematically here and is designed to carry out the method according to the invention. Provision is further made for a display device 10 comprising a plurality of monitors 11, on which a representation 12 of a location-dependent dosage value on the surface of the patient 8 can be shown in addition to recorded images and/or recording parameters. Recording parameters can be entered and the components of the X-ray device 1 can be repositioned by means of an operating device 13, which is likewise shown only schematically. Finally, as a measuring means, the exemplary X-ray device 1 shown here comprises a camera 14 for measuring position, orientation and surface of the patient 8. Alternatively or additionally, provision can also be made for ultrasound sensors and/or similar.

The control device 9 is additionally in contact (via a network) with an information system 15, a radiology information system in this case, from which data relating to the next examination and/or the patient 8 can be retrieved.

An internal calibration of the individual components of the X-ray device 1 also takes place. The position of the C-arm 3 relative to the patient support plate 7 and the camera 14 is therefore essentially known. In practical terms, these recording parameters are continuously available to the control device 9.

As mentioned above, taking into consideration parameters that describe the recording geometry and the radiation that is administered, the control device 9 is inventively designed to determine a location-dependent dosage value on the surface of the patient 8, said surface being described by a patient model, to generate a representation of the dosage value (and/or a value that is derived therefrom) on this basis, and to depict this on the display device 10. It is therefore necessary firstly to determine the parameters describing the recording geometry and the radiation that is administered. For this, consideration is given to recording parameters/settings that are intrinsically present in the X-ray device 1, namely the position and orientation of the radiation source 4 in this case. On this basis of the internal calibration, it is then possible to infer the position and orientation of the patient support plate 7 relative to the radiation source 4, the opening angle of the radiation source 4 and optionally a collimation of the radiation source 4 if provision is made for this. In order to determine the relative position and orientation of patient 8 and radiation source 4, these being subsequently used to ascertain the recording geometry and the irradiated surface of the patient, the position and orientation of the patient 8 relative to the patient support plate 7 must therefore also be established, and this can be done by means of the camera 14 or, more precisely, by analyzing its image signals. It should be noted at this point that it is obviously also possible to directly ascertain e.g. the position of the patient 8 relative to the radiation source 4, or even to omit the camera 14, in order to make assumptions concerning the position and the orientation of the patient 8, possibly supported by recording parameters that are entered e.g. during the patient registration.

In this case, a patient model is used in which the surface of the patient will be described by ellipsoids (head, torso) and cylinders (extremities). This patient model can be adapted in a patient-specific manner e.g. by taking into consideration patient-specific information which can be obtained from the information system 15 or entered via the operating device 13, namely the size, weight, sex and age of the patient 8 in this case. In principle, it is obviously also conceivable to further adapt the patient model with reference to data from the camera 14, which already determines the position and orientation of the patient 8, or to determine the patient model entirely on the basis of such data. It should also be noted that models/measurements of the surface of the patient can obviously be made with any desired degree of accuracy.

Once the position and orientation of the patient model relative to the patient support plate 7 and hence to the radiation source 4 are known, and the radiation fan beam of the radiation source 4 can be ascertained on the basis of the opening angle and optionally the collimator properties, it is also possible to determine which region of the surface of the patient 8 is affected by the radiation of the radiation source 4. This is explained in greater detail by FIG. 2.

Figure 2:
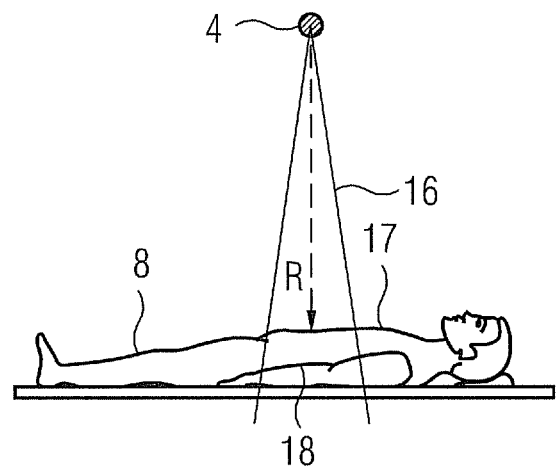
FIG. 2 shows a diagram of the recording geometry.

In FIG. 2, the radiation source 4 is depicted as a point and the radiation fan beam 16 is shown. It can be seen in this example that parts of the torso 17 and arm 18 of the patient 8 are irradiated. If the radiation characteristics of the radiation source 4 are also known, the $1/R^2$ law (as shown in FIG. 2, R represents the distance from the radiation source 4 to the surface of the patient 8) can be applied in order to determine the location-dependent dosage value, i.e. the skin dosage for the irradiated regions. In order to achieve this, provision can be made e.g. for subdividing the radiation fan beam 16 and/or the irradiated region into subareas/subregions, for which a dosage value is then ascertained in each case.

The radiation characteristics of the radiation source 4 are measured in the present example of the X-ray device 1, specifically by means of a dosage measuring device 19 which measures the dosage area product. The dosage value on the surface of the patient 8 can be determined by dividing by the subareas for instance.

Of course, it is also possible to ascertain the radiation characteristics or dosage characteristics of the radiation source 4 for a recording automatically from operating parameters or recording parameters of the radiation source 4, in particular from the operating voltage of the radiation source 4, from a total current of the radiation source 4 for the recording and, if filtering is present, taking into consideration prefiltering parameters which describe said filtering. It is also then possible to determine the location-dependent dosage value for the recording geometry and recording on the basis of the standard relationships.

It should be noted at this point that is it also possible to ascertain a plurality of location-dependent dosage values, which are then assigned to different radiation energies and/or radiation energy ranges. Observation in various regions of the X-ray spectrum is also possible. From this, it is then possible to determine e.g. an average energy of the radiation occurring at a specific location on the surface of the patient. The average energy and/or the plurality of dosage values can then be shown in the same way, in particular a plurality of these variables can also be shown concurrently, thereby providing a comparison and information which is as comprehensive as possible.

During an examination or when monitoring an intervention, the X-ray device 1 usually carries out a plurality of recordings. In this case, the location-dependent total dosage value is observed, i.e. the location-dependent dosage value for this recording is determined in real time after each recording, whereupon this dosage value of the last recording is added to the dosage values of the previous recordings. The representation 12 is updated at the same time. The development of the skin dosage during the examination/intervention can therefore be continuously displayed, such that adaptations can be carried out by the user if applicable.

Of course, it is also possible to calculate the total dosage value completely or partially in advance, e.g. if all recordings are already planned in advance or if the effect of a further recording, carried out in real time, is to be observed. This can be configured as appropriate by a user via the operating device 13, for example.

If such a total dosage value has been ascertained, provision is made for continuously monitoring the position and orientation of the patient 8 by means of the camera 14, in order to detect and take into consideration any changes. Therefore movements of the patient between the recordings can also be determined and taken into consideration.

Figure 3:
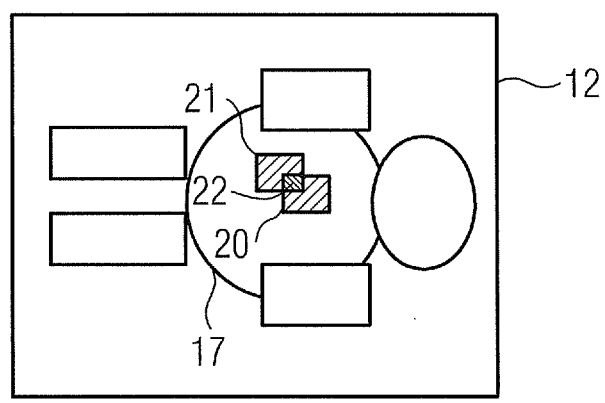
FIG. 3 shows a possible representation of the dosage value.

FIG. 3 shows an exemplary representation 12 of the total dosage value. A view onto the surface of the patient 8 can be seen. In the present case, for the sake of simplicity, only two recordings having the same radiation characteristics are carried out in the region of the torso 17, wherein their irradiation fields 20, 21 overlap in a region 22 in which a higher total dosage value (i.e. a higher skin dosage) is consequently present. This is shown by means of color coding in the present case, i.e. a high total dosage value is depicted in red and a low total dosage value is depicted in blue. Of course, other color scales are also conceivable.

The representation initially takes place in such a way that a view is principally shown from the current irradiation direction (projection direction). This "virtual irradiation direction" can be changed by a user by means of a joystick 23 which is provided on the operating device 13 as an operating element, but a change can also be effected by moving the C-arm 3 itself, such that the current irradiation direction changes. A user can optionally switch between different modes.

It is noted that other types of representation, e.g. a rendered 3D representation, are obviously also possible.

Finally, it should be noted that the method according to the invention can also be applied to X-ray devices comprising a plurality of radiation sources by performing and taking into consideration the calculations for each radiation source in this case. If applicable, a representation from a plurality of (in particular both) irradiation directions is possible for e.g. a biplanar X-ray device. These representations are displayed concurrently.

The invention claimed is:

1. A method for monitoring an X-ray dosage administered to a patient by a radiation source when recording an image using an X-ray device, comprising:
    describing a recording geometry by parameters;
    describing a surface of the patient by a patient model, wherein said surface corresponds to an irradiated skin surface;
    determining a location-dependent skin dosage value on the surface as a sum of skin dosage values for a plurality of recordings; and
    displaying a representation of the skin dosage value.

2. The method as claimed in claim 1, wherein a relative position and orientation of the patient, a radiation source, and a radiation fan beam of the radiation source are determined from the parameters describing the recording geometry.

3. The method as claimed in claim 1, wherein the recording geometry is described by the parameters selected from the group consisting of: a position and orientation of the radiation source, an opening angle of the radiation source, a collimation of the radiation source, a position and orientation of a patient support plate relative to the radiation source, a position and orientation of the patient, the surface of the patient, and combinations thereof.

4. The method as claimed in claim 3,
    wherein the position and orientation of the patient, the position and orientation of the radiation source, and/or a position and orientation of the patient relative to the patient support plate are determined in a same coordinate system, and
    wherein the position of patient support plate relative to the radiation source is derived from an internal calibration of the X-ray device.

5. The method as claimed in claim 1, wherein the parameters are measured or derived from recording parameters.

6. The method as claimed in claim 5, wherein a dosage characteristic of the radiation source is determined from an operating voltage of the radiation source, a total current of the radiation source, and/or a prefiltering parameter.

7. The method as claimed in claim 5, wherein a dosage area is measured by a measuring device arranged at the radiation source.

8. The method as claimed in claim 3, wherein the position and orientation of the patient is measured optically by a camera, or by ultrasound.

9. The method as claimed in claim 1, wherein the patient model comprises a cylinder, or an ellipsoid.

10. The method as claimed in claim 9, wherein the patient model is adapted with reference to patient-specific information selected from the group consisting of: size of the patient, weight of the patient, sex of the patient, age of the patient, and combinations thereof.

11. The method as claimed in claim 10, wherein the patient-specific information is obtained from an information system or a patient registration.

12. The method as claimed in claim 1, wherein a movement of the patient between the recordings is determined.

13. The method as claimed in claim 1, wherein the skin dosage values are determined for various radiation energies or radiation energy ranges.

14. The method as claimed in claim 13, wherein an average energy of the various radiation energies, or radiation energy ranges is determined as a derived value.

15. The method as claimed in claim 1, wherein the representation of the skin dosage values is displayed by a view from a current irradiation direction, or an irradiation direction of a current setting of the X-ray device.

16. The method as claimed in claim 1, wherein a viewing direction of the representation is changed by a user with an operating element.

17. The method as claimed in claim 1, wherein the representation is a 3D representation.

18. The method as claimed in claim 1, wherein the representation is color-coded.

19. The method according to claim 3, wherein, for a particular recording, the location-dependent skin dosage value on the surface is determined based on an average distance of the surface from a focus of a radiation source of the X-ray device.

* * * * *